United States Patent [19]
Willer et al.

[11] Patent Number: 5,380,777
[45] Date of Patent: Jan. 10, 1995

[54] POLYGLYCIDYL NITRATE PLASTICIZERS

[75] Inventors: Rodney Willer, Newark, Del.; Alfred G. Stern, Elkton, Md.; Robert S. Day, Newark, Del.

[73] Assignee: Thiokol Corporation, Ogden, Utah

[21] Appl. No.: 224,098

[22] Filed: Mar. 28, 1994

Related U.S. Application Data

[62] Division of Ser. No. 2,423, Jan. 8, 1993, abandoned.

[51] Int. Cl.⁶ .................. C07C 203/04; C08G 59/14; C08K 5/32; C08L 71/02
[52] U.S. Cl. .................. 524/186; 525/526; 525/403; 528/418; 558/480; 568/589; 568/620; 524/429
[58] Field of Search ............... 525/526, 403; 568/589, 568/620; 558/480; 528/418; 524/186, 429

[56] References Cited

U.S. PATENT DOCUMENTS

| | | |
|---|---|---|
| 2,198,367 | 5/1940 | Jacobi . |
| 3,557,181 | 1/1971 | Lakritz . |
| 3,680,483 | 8/1972 | Staudacher et al. . |
| 3,811,358 | 5/1974 | Morse . |
| 3,870,578 | 3/1975 | Nichols, Jr. . |
| 4,268,450 | 5/1981 | Frankel et al. . |
| 4,478,656 | 10/1984 | Gibson ........................ 524/199 |
| 4,799,980 | 1/1989 | Reed, Jr. ..................... 524/186 |
| 4,820,859 | 4/1989 | Millar et al. . |
| 5,120,827 | 6/1992 | Willer et al. . |

FOREIGN PATENT DOCUMENTS

| | | |
|---|---|---|
| WO/9001028 | 2/1990 | WIPO . |
| WO/9015092 | 12/1990 | WIPO . |
| WO/9015093 | 12/1990 | WIPO . |

OTHER PUBLICATIONS

Colclough, Eamon, et al., Novel Energetic Monomers and Polymers Prepared Using Dinitrogen Pentoxide Chemistry; Joint International Symposium on Compatibility of Plastics and other Materials with Explosives, Propellanats, Pyrotechnics and Processing of Explosives, Propellants and Ingredients, 23–25 Oct. 1989, Virginia Beach, Virginia.

Willer, Rodney L., et al., Poly(Glycidyl Nitrate) Revisited, American Defense Assn Intn'l Symposium on Compatibility of Plastics and Other Materials with Explosives, Propellants and Pyrotechnics and Processing Propellants, Explosives and Ingredients, Virginia Beach, Va. 23–25 Oct. 1989.

Primary Examiner—Melvyn I. Marquis
Assistant Examiner—D. R. Wilson
Attorney, Agent, or Firm—Cushman, Darby & Cushman

[57] ABSTRACT

This invention is first, a difunctional poly(glycidyl nitrate) oligomer (PGN oligomer), second, nitrated PGN oligomer and third, the use of the nitrated PGN oligomer as a plasticizer, particularly as a plasticizer for binders used in and/or as energetic formulations. Examples of energetic formulations are propellants, pyrotechnics and explosives and other such compositions. More particularly, this invention is a difunctional poly(glycidyl nitrate) oligomer of the formula

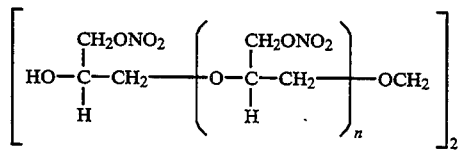

where n is 0 to 3, having a $M_n$ of from about 304 to about 994. Another embodiment is the nitrated difunctional poly(glycidyl nitrate) oligomer of the formula

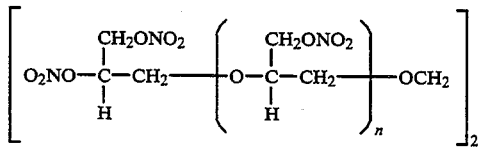

where n is 0 to 3, having a $M_n$ of from about 394 to about 1084. This invention also comprises a plasticizer for binder compounds, namely, the nitrated PGN oligomer above; preferably the plasticizer above is used wherein the binder compound is used in energetic formulations; and preferably the binder compound is an energetic compound; more preferably the energetic formulation is selected from the group consisting of propellants, pyrotechnics and explosives.

6 Claims, 1 Drawing Sheet

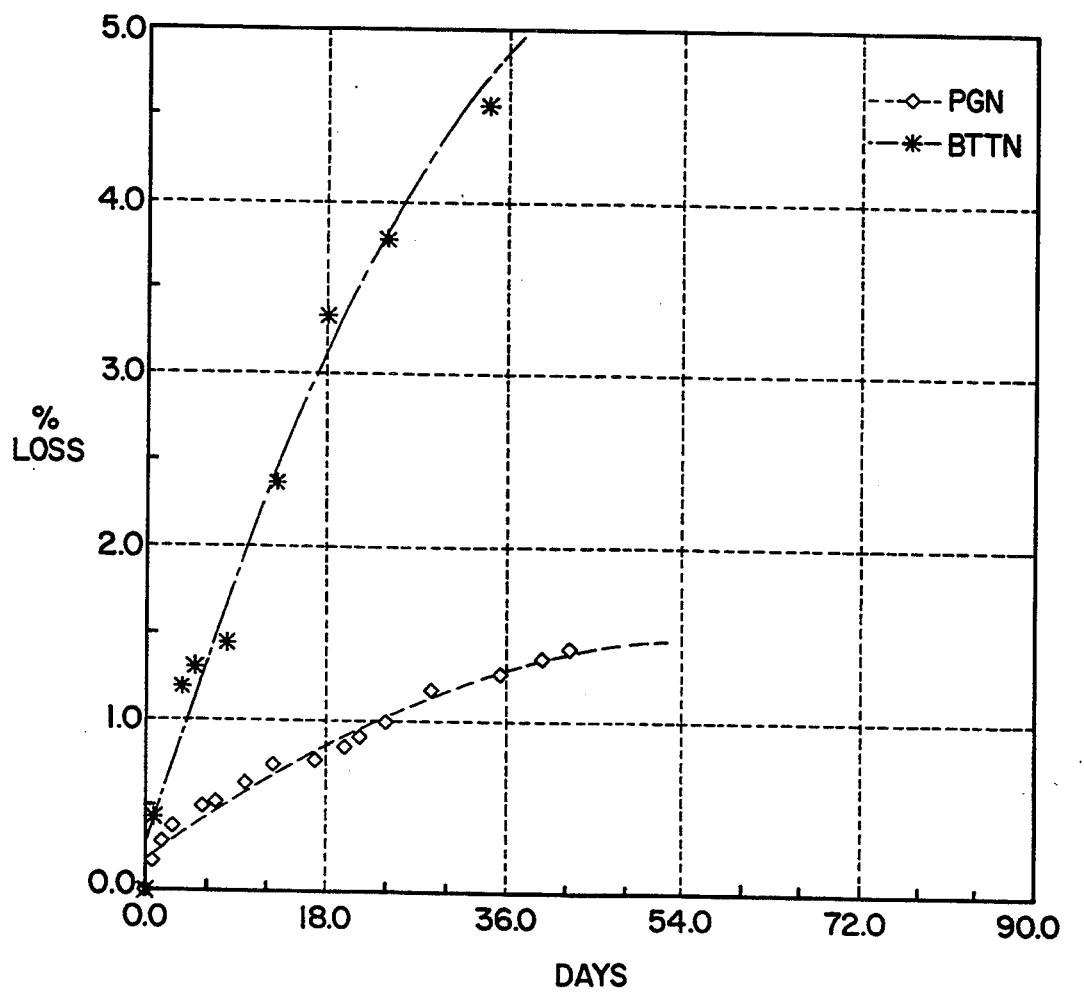

POLYGLYCIDYL NITRATE PLASTICIZERS

This is a division of application Ser. No. 08/002,423, filed on Jan. 8, 1993, abandoned.

BACKGROUND OF THE INVENTION

1. Field of the Invention

This invention relates to poly(glycidyl nitrate) plasticizers and their use in energetic formulations.

2. Description of the Prior Art

Poly(glycidyl nitrate) (PGN) is an energetic polymer structurally related to the well known glycidyl azide polymer (GAP). Although they are structurally similar, PGN and GAP are synthesized by different routes. GAP is synthesized by first polymerizing epichlorohydrin (ECH) (e.g., glycidyl chloride) to poly(epichlorohydrin) (PECH), then the PECH is converted to GAP by reaction with sodium azide in dimethylsulfoxide. PGN, on the other hand, is synthesized by first converting ECH to glycidyl nitrate (GN) by a two-step procedure; then the GN is polymerized to PGN. Because of the cheaper reagents used in the synthesis and the simpler synthetic scheme employed, PGN would be potentially much cheaper to produce than GAP.

Although most recent work on energetic polymers has centered on GAP and various poly(oxetanes), PGN was in fact the first energetic prepolymer investigated. The initial work on PGN was done by Thelen et al in the 1950's at the Naval Ordnance Test Station (NOTS, now NWC). They studied the polymerization of glycidyl nitrate by a variety of Lewis acid catalysts with most of the work centering on the use of stannic chloride ($SnCl_4$) as the catalyst. No propellants were prepared by the NOTS workers and they noted that one drawback to their synthesis was the laborious purification procedure.

PGN and PGN propellants were next examined at the Jet Propulsion Laboratory (JPL). The JPL workers found that PGN made using boron trifluoride etherate was low in both functionality (i.e., 2) and molecular weight ($M_n = 1500$) and therefore polyurethane propellants made from this PGN had poor mechanical properties. Similar observations were made by other workers. In summary, it has long been recognized that PGN would be an excellent energetic polymer but until now a method of synthesis could not be found that would produce nearly difunctional material with acceptable hydroxyl equivalent weights.

The synthesis is described in allowed U.S. Pat. No. 5,120,827 hereby incorporated by reference, in toto.

SUMMARY OF THE INVENTION

This invention is first, a difunctional poly(glycidyl nitrate) oligomer (PGN oligomer), second, nitrated PGN oligomer and third, the use of the nitrated PGN oligomer as a plasticizer, particularly as a elasticizer for binders used in and/or as energetic formulations. Examples of energetic formulations are propellants, pyrotechnics and explosives and other such compositions.

More particularly, this invention uses a difunctional poly(glycidyl nitrate) oligomer of the formula

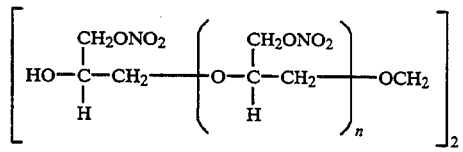

where n is 0 to 3, having a $M_n$ of from about 304 to about 994.

Another embodiment is the nitrated difunctional poly(glycidyl nitrate) oligomer of the formula

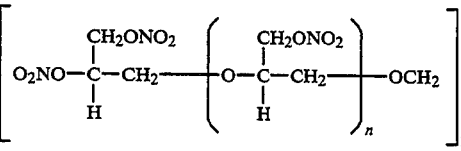

where n is 0 to 3, having a $M_n$ of from about 394 to about 1084.

This invention also comprises a plasticizer for binder compounds which comprises the nitrated PGN oligomer above; preferably the plasticizer above is used wherein the binder compound is used in energetic formulations; and preferably the binder compound is an energetic compound; more preferably the energetic formulation is selected from the group consisting of propellants, pyrotechnics and explosives.

Preferably the binder compound is selected from the group consisting of poly(glycidyl nitrate), poly(ethylene glycol), poly(diethylene glycol adipate), glycidyl azide polymer, poly(caprolactone), poly(propylene glycol), poly(neopentyl glycol) adipate, poly(nitratomethyl methyl oxetane), and other energetic polyoxetanes. It is preferred that the binder compound is a difunctional poly(glycidyl nitrate) having a $M_n$ of at least 1500, and preferably the poly(glycidyl nitrate) has a $M_n$ of from about 2,000 to about 4,000. This invention also comprises a method of plasticizing binder compounds comprising adding the nitrated PGN oligomer to the binder compound by mixing a portion of that oligomer with a portion of the binder compound, then using the binder in an energetic formulation. Preferably the oligomer is added in a ratio of about 2 to about 0.25 oligomer to binder compound.

BRIEF DESCRIPTION OF THE DRAWING

FIG. 1 is a graph comparing the volatility of the PGN nitrate plasticizer of this invention to that of 1,2,4-butane trioltrinitrate (BTTN).

DETAILED DESCRIPTION OF THE PREFERRED EMBODIMENTS

Difunctional PGN oligomer was prepared using a procedure similar to the one disclosed in U.S. Pat. No. 5,120,827 incorporated by reference above. This prior procedure produced a normal molecular weight PGN, $M_n$ about 2800 a.m.u. By the procedure of this invention glycidyl nitrate was polymerized using $HBF_4$ catalyst and ethylene glycol initiator to produce a lower molecular weight, difunctional PGN prepolymer ($M_n = 994$ a.m.u.) as shown in equation 1. This material was then nitrated with acetic anhydride and nitric acid to give the desired PGN plasticizer (equation 2).

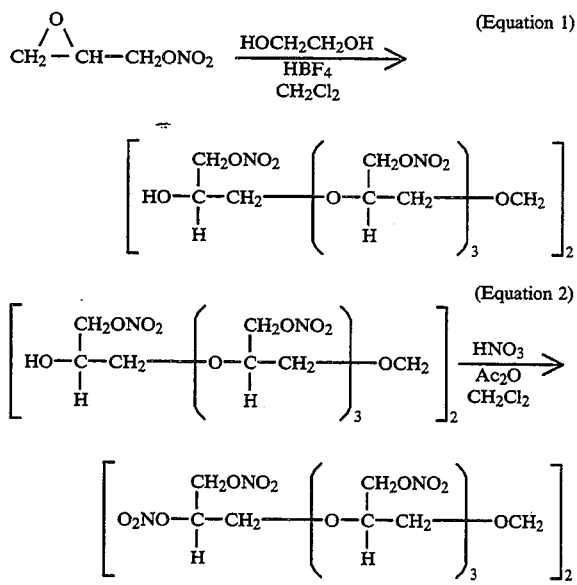

EXAMPLE 1

Preparation of Low Molecular Weight Polyglycidyl Nitrate (PGN)

Tetrafluroboric acid dietherate (43.7 mL, 47.6 g, 0.25 mol, Aldrich) was added, via syringe, to rapidly stirred ethylene glycol (13.8 mL, 15.5 g, 0.25 mol, Aldrich) under $N_2$. The $HBF_4 \cdot OEt_2$ addition was maintained so as not to exceed a reaction temperature of 27° C. After the addition was complete, the solution was allowed to stir for 1h and the ether was removed under high vacuum (18h). The resulting viscous residue was then dissolved in anhydrous $CH_2Cl_2$ (915.0 mL, Aldrich) and this solution was cooled to 11° C. A solution of glycidyl nitrate (238 g, 2.0 mol, >98% purity) in anhydrous $CH_2Cl_2$ (160 mL) was then added dropwise to the catalyst-initiator/$CH_2Cl_2$ solution at a rate so as to maintain a reaction temperature of 13°±2° C. After the addition was complete (113 min total addition time), the progress reaction was checked by $^1$H-NMR (60 MHz, $CHCl_3$). The disappearance of the signals due to GN (i.e., δ3.27, 2.90 and 2.71) and the appearance of signals due to PGN (at δ4.60 and 3.80) indicated the reaction was complete. The mixture was then quenched with brine (85 mL) and was washed with saturated aqueous $NaHCO_3$ (3×100 mL). The organic fraction was dried over anhydrous $MgSO_4$, was filtered, and the $CH_2Cl_2$ was evaporated in vacuo to afford PGN (250.3 g, 99%) as a viscous light yellow liquid. DSC (mp−36.1° C.). GPC (THF, polystyrene standards); Mw=1307; Mn=944; Mw/Mn=1.39. Hydroxy equivalent weight=439 g/eq. Functionality$^9 \geq$ 2.05. Viscosity=107 poise. IR (NaCl) 3448 (m), 2920 (m), 1736 (w), 1632 (s), 1272 (s), 1128 (m), 1000 (m), 856 (s) cm$^{-1}$. NMR ($CDCl_3$, 60 MHz) δ5.30 (br.s, 1.3H), (m, 16H), 4.25–3.20 (m, 28H).

Anal. calcd. for $C_{3.25}H_{5.75}N_{1.00}O_{4.25}$: C, 30.78; H, 4.57; N, 11.04. Found: C, 30.83; H, 4.72; N, 11.13.

EXAMPLE 2

Preparation of Low Molecular Weight PGN Plasticizer by Acetic Anhydride/Nitric Acid Nitration 100% $HNO_3$ (11.48 g, 182.2 mmol, distilled) was added dropwise to acetic anhydride (17.2 mL, 182.2 mmol) at 15° C. under nitrogen. The nitric acid addition rate was controlled so as not to exceed a reaction temperature of 20° C. After the addition was complete, the mixture was allowed to stir at 15° C. for 30 minutes. The mixture was then cooled to −10° C. and was added to a stirred solution of PGN (20.0 g, 19.7 mmol, 438 hydroxyl equivalent weight, Lot D121) and $CH_2Cl_2$ (35 mL) cooled to −10° C. under $N_2$. Acetyl nitrate solution was added at such a rate so as not to exceed a reaction temperature of −5° C. After the addition was complete, the reaction mixture was allowed to stir at 4°–5° C. (under $N_2$) for 2h. The solution was poured onto ice $H_2O$ (125 mL) and the mixture was extracted with methylene chloride (3×75 mL). The combined $CH_2Cl_2$ extract was washed with saturated aqueous $NaHCO_3$ (2×25 mL), was dried over $MgSO_4$, and the solvent was evaporated in vacuo. The residue was dried under high vacuum to give the PGN plasticizer (19.7 g, 91%) as a yellow liquid. DSC (Tg=−40.1° C.). GPC (THF, polystyrene standard); Mw=1310; Mn=955; Mw/Mn=1.37. IR (NaCl). 2936 (w), 1736 (w), 1672 and 1640 (s), 1296 (s), 1128 (m), 1000 (m), 856 (s) cm$^{-1}$. $^1$H-NMR (300 MHz, $CDCl_3$) δ5.4 (s, 2H), 4.95–4.30 (m, 16H), 4.10–3.25 (m, 26H).

Anal. calcd. for $C_{2.6}H_{4.4}N_{1.0}O_{3.8}$: C, 28.27; H, 4.02; N, 12.68. Found: C, 28.37; H, 4.02; N, 12.36.

Hydroxyl Equivalent Weight=28,870 g/eq

EXAMPLE 3

Preparation of Low Molecular Weight PGN Nitrate Plasticizer by $N_2O_5$ Method

Low molecular weight PGN (53.0 g, 52.2 mmol, 414 hydroxyl equivalent weight, lot D-135) was mixed with dry methylene chloride (110 ml, 1.29 moles) at ambient temperature under $N_2$ for 30 minutes. The mixture was then cooled to 0° C. and a 1M solution of $N_2O_5$ in Dry $CH_2Cl_2$ (277 g) was added over 31 minutes so as not to exceed a reaction temperature of +4° C. After the addition was complete, the mixture was allowed to stir at 2°–9° C. for 4h. The solution was poured onto ground ice (500 g) and stirred until all the ice melted. The aqueous and organic layers were separated. The organic layer was washed with saturated aqueous $NaHCO_3$ (2×385 ml), and dried over $Na_2SO_4$. The solution was then stired with decolorizing carbon for one hour, filtered, and the solvent was evaporated in vacuo. The residue was dried under high vacuum to give PGN plasticizer (56.2 g, 97.9%).

DSC, (Tg)−47.1° C. GPC (THF, polystyrene standard); MW=1182; Mn=939; Mw/Mn=1.26. IR (NaCl), 2903 (w), 1670 and 1637 (s), 1278 (s), 1122 (m), 966 (m), 849 (s) cm$^{-1}$.

$^1$H-NMR (60 MHz, $CDCl_3$) δ5.4 (s, 2H), 4.80–4.50 (m, 16H), 4.00–3.60 (m, 26H). Viscosity=0.4 poise.

Anal. calcd. for $C_{2.6}H_{4.4}N_{1.0}O_{3.8}$: C, 28.27; H, 4.02; N, 12.68, Found: C, 27.99; H, 4.04; N, 12.69

Hydroxyl equivalent weight=23,110 g/eq

EXAMPLE 4

The following is an example of the use of the PGN nitrate plasticizer in a propellant. Table 1 shows the compostion of two 70% solids PGN/AN propellants. The baseline propellant, column 1, is an unplasticized version while the second propellant, column 2, has 5.00 wt % of the PGN nitrate plasticizer replacing PGN binder. The plasticized propellant has a reduced stress and modulus values, increased strain, a lower EOM viscosity and a lower Tg.

TABLE 1

| Baseline Propellant PGN Nitrate Plasticized Propellant | 1 | 2 |
|---|---|---|
| PGN | 26.82 | 22.29 |
| PGN Nitrate | | 5.00 |
| Desmodur N-100 (Lot E109) | 1.95 | 1.62 |
| HMDI | 0.83 | 0.69 |
| TPB | 0.03 | 0.03 |
| MNA | 0.37 | 0.37 |
| AN, 200μ | 49.0 | 49.0 |
| AN, 20μ | 21.0 | 21.0 |
| EOM Viscosity, | 12 | 8 |
| | (117° F.) | (114° F.) |
| Stress (max), psi | 157 | 118 |
| Stress (rupture), psi | 149 | 108 |
| Strain (at max stress), % | 29 | 43 |
| Strain (at rupture), % | 32 | 49 |
| Modulus$^{2.6}$, psi | 901 | 483 |
| Tg, °C. | −24.6 | −28.8 |

The change in some mechanical properties could be achieved by reducing the cure agent to polymer ratio. However, the change in the EOM viscosity and Tg can only be obtained by incorporation of a plasticizer. More important is the much lower volatility of the plasticizer of this invention.

The desirable reduced volatility of the PGN nitrate plasticizer relative to other nitrate ester platicizers can best be illustrated by the vacuum aging data summarized in FIG. 1. This figure shows a plot of the percent weight loss of a sample of the PGN nitrate plasticizer and a sample of BTTN versus time at an average vacuum of 0.2 mm. This vacuum is equivalent to an altitude of greater than 205,000 ft or thirty-eight (38) miles. The PGN nitrate loses very little weight >2% in 43 days while the BTTN has suffered a substantial weight loss in the same time period. BTTN is 1,2,4-butanetriol trinitrate.

This PGN plasticizer offers a number of advantages over traditional nitrate ester plasticizers (e.g., TEGDN, TMETN, BTTN, etc.). These advantages would include: excellent miscibility with normal molecular weight PGN; low volatility; a low Tg (ca−40° C.) relative to normal molecular weight PGN (−23° to −26° C.); decreased plasticizer motility; and excellent enthalpies of combustion and explosion characteristics.

Related prior art compounds were unsuited as plasticizers because they had too high viscosity for improved processing and usually had functional terminal groups. The end groups in these inventive compounds are nitrated and not functional. The inventive compounds provide a low viscosity, low volatility, energetic plasticizer compound.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A nitrated difunctional poly(glycidyl nitrate) oligomer of the formula

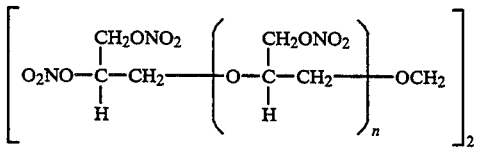

where n is 0 to 3, having a $M_n$ of from about 394 to about 1084.

2. A composition which comprises:
   (A) a plasticizer which comprises a nitrated difunctional poly(glycidyl nitrate) oligomer of the formula

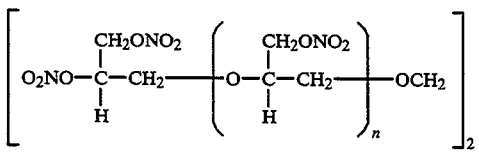

where n is 0 to 3, having a $M_n$ of from about 394 to about 1084, and
   (B) a binder compound selected from the group consisting of poly(glycidyl nitrate), poly(ethylene glycol), poly(diethylene glycol adipate), glycidyl azide polymer, poly(caprolactone), poly(propylene glycol), poly(neopentyl glycol) adipate, poly(nitratomethyl methyl oxetane), and other energetic polyoxetanes.

3. The composition according to claim 2, wherein the binder is a poly(glycidyl nitrate).

4. The composition according to claim 2, wherein the poly(glycidyl nitrate) is a difunctional poly(glycidyl nitrate) having a $M_n$ of at least 1500.

5. The composition according to claim 4, wherein the difunctional poly(glycidyl nitrate) has a $M_n$ of from about 2,000 to about 4,000.

6. The composition according to claim 2, wherein said composition further comprises ammonium nitrate.

* * * * *